United States Patent [19]

Kitajima et al.

[11] 4,255,384
[45] Mar. 10, 1981

[54] MULTILAYERED INTEGRAL ELEMENT FOR THE CHEMICAL ANALYSIS OF THE BLOOD

[75] Inventors: Masao Kitajima; Fuminori Arai; Asaji Kondo, all of Osaka, Japan

[73] Assignee: Fuji Photo Film Co., Ltd., Minami-ashigara, Japan

[21] Appl. No.: 66,363

[22] Filed: Aug. 14, 1979

[30] Foreign Application Priority Data

Aug. 14, 1978 [JP] Japan .................................. 53/98900
Aug. 14, 1978 [JP] Japan .................................. 53/98902

[51] Int. Cl.³ .............................................. G01N 31/22
[52] U.S. Cl. ........................................ 422/57; 422/56; 422/58
[58] Field of Search .............................. 422/56, 57, 58

[56] References Cited

U.S. PATENT DOCUMENTS

| | | | |
|---|---|---|---|
| 3,511,608 | 5/1970 | Anderson | 422/56 |
| 3,526,480 | 9/1970 | Rindl et al. | 422/66 |
| 3,663,374 | 5/1972 | Moyer et al. | 435/4X |
| 3,874,995 | 4/1975 | Stroterhoff | 422/56 X |
| 3,992,158 | 11/1976 | Przybylowicz et al. | 422/57 |
| 4,042,335 | 8/1977 | Clement | 422/56 |
| 4,050,898 | 9/1977 | Goffe et al. | 422/57 |
| 4,066,403 | 1/1978 | Bruschi | 422/57 X |

*Primary Examiner*—Barry S. Richman
*Attorney, Agent, or Firm*—Sughrue, Rothwell, Mion, Zinn and Macpeak

[57] ABSTRACT

An integral multilayered element for the chemical analysis of the blood comprising a combination of a porous spreading layer, a reagent layer, and a radiation-blocking layer, said radiation-blocking layer being water-permeable and containing at least one elemental metal or an alloy thereof.

16 Claims, 5 Drawing Figures

MULTILAYERED INTEGRAL ELEMENT FOR THE CHEMICAL ANALYSIS OF THE BLOOD

BACKGROUND OF THE INVENTION

1. Field of the Invention

This invention relates to a multilayered integral element for the chemical analysis of the blood, and in particular to an element which permits the assay of whole blood, plasma or serum for quantitative analysis of the chemical components of the blood.

2. Description of the Prior Art

Blood samples for use in analyzing the chemical components of blood include whole blood and the fluid part of the blood, i.e., plasma and serum, which are obtained after the laborious operation of removing the colored definitely-shaped components of blood. Needless to say, it would be convenient and desirable to employ a process which permits the use of whole blood per se for simple and rapid quantitative analysis of blood or rush assay of blood, e.g., in emergency cases.

Due to technical difficulties, there has not heretofore been provided a method and an analytical material for chemical quantitative analysis of blood which employs whole blood as the assay sample and which is a simple, rapid and dry method.

Multilayered integral elements for the simple and rapid dry quantitative chemical analysis of the blood which are characterized by a porous spreading layer have been disclosed in, for example, Japanese Patent Application (OPI) Nos. 53888/74, 137192/75, 40191/76 (U.S. Pat. No. 4,042,335, 3488/77 (U.S. Pat. No. 4,066,403), 131786/77 (U.S. Pat. No. 4,050,898), and 24893/78, U.S. Pat. Nos. 3,992,158, 3,526,480 and 3,663,374 and collected papers by J. N. Eikenberry et al from the 10th International Meeting of Clinical Chemistry (Mexico City, Feb. 26 through Mar. 3, 1978). The fundamental construction of these elements as described in U.S. Pat. No. 4,042,335 is the combination of a porous spreading layer and a reagent layer, the latter sometimes being a multilayered unit in which its functions are divided into, for example, a first reagent layer and a second reagent layer or a color developing, color detecting or color receiving layer. Sometimes an intermediate layer called a radiation-blocking layer or a barrier layer is placed between such a plurality of reagent layers. Alternatively, there has been provided a construction in which the spreading layer includes a reagent and thus the spreading and reagent layers are integrated. In any case, these elements are based on the two functional layers, i.e., the spreading layer and the reagent layer.

A blood sample dropped on this type of elements for the chemical analysis of blood diffuses uniformly throughout the porous spreading layer and permeates into the reagent layer through its surface. Since the reagent layer has a system incorporated therein, which, upon reaction with the particular component in blood, ultimately leads to a reaction of color development, coloration or discoloration, the components of blood can be quantitatively analyzed by colorimetry, densitometry, fluorimetry, etc.

Since these known multilayered integral elements for the chemical analysis of the blood are described as applicable to whole blood as well as to serum in the above-mentioned references, tests were conducted using whole blood which revealed that the thickness of the radiation-blocking layer must be about 150 $\mu$m or more in order to impart an acceptable radiation-blocking ability since the radiation-blocking material taught in the references chiefly comprises a white pigment and even this thickness is not adequate when the system is wet. It was also found that with an increase in the thickness of the system, its permeability to blood is remarkably affected in addition to the inconvenience in manufacture.

SUMMARY OF THE INVENTION

As a result of extensive studies to overcome the difficulties with prior art radiation-blocking layers it has been discovered that a radiation-blocking layer having good permeability to water containing a metal and particularly a metal film or a metal powder is most effective for the chemical analysis of whole blood samples.

Therefore, a principal object of the present invention is to provide a multilayered integral element for the quantitative chemical analysis of the blood using whole blood as a sample.

Another object of the present invention is to provide a rapid and simple dry method for the quantitative chemical analysis of the blood.

Still another object is to provide such a multilayered integral element for the chemical analysis of the blood which permits a colored reagent to be incorporated therein as an analytical reagent.

Thus the present invention provides:

In a multilayered integral element for the chemical analysis of the blood comprising a combination of a porous spreading layer and a reagent layer, the improvement wherein said element comprises a water-permeable metal-containing radiation-blocking layer.

In another embodiment of the invention, the multilayered integral element for the chemical analysis of the blood further comprises a support for lending additional structural integrity to the multilayered integral element.

DETAILED DESCRIPTION OF THE INVENTION

Figure 1:
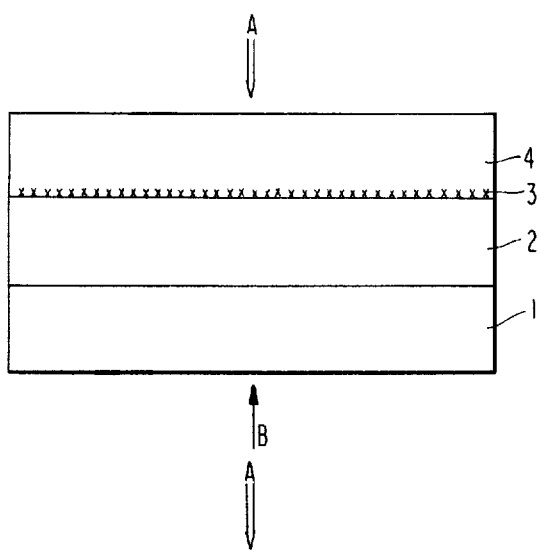
FIGS. 1 to 4 are cross-sections of multilayered integral elements for the chemical analysis of the blood in accordance with the present invention.

The water-permeable radiation-blocking layer of the present invention is characterized by the presence of a metal. The metal may be in the form of a metal film or a layer of a metal powder. The layer performs essentially two functions depending upon its construction and its location within the multilayered integral element of the present invention. The radiation-blocking layer serves to block light transmitted from the porous spreading layer side of the element and as a reflective surface for the colorimetric analysis. The radiation-blocking layer is positioned within the element such that it does not interfere with reading the chemical analysis. Thus, it can be positioned any place in the element as long as it is not between the layer in which the color change is registered and the observation side of the element. For example, the radiation-blocking layer can be formed on either surface of the porous spreading layer in an element of the type shown in FIGS. 1 or 3 wherein the reagent layer is adjacent the observation side of the element. In more preferred embodiments of the invention, where the function of the reagent layer is divided such that the color forming reaction takes place in one layer (the reagent layer) and the color is registered or detected in another layer (the detecting layer), the radiation-blocking layer is usually located between the reagent layer and the detecting layer such that the color of the reagent layer or the blood is blocked from the colorimetric analysis of the detecting layer. These embodiments of the invention and locations of the radiation-blocking layer will become more clear from the following detailed discussion.

The metal-containing radiation-blocking layer in accordance with one embodiment of the present invention is a thin metal film having a thickness of about 1,000 A or less. Since it is difficult to fabricate it independently a porous sheet is generally employed as a support on which the metal film is formed.

The metal film of the present invention is not a flat film without pinholes but is full of pinholes in a microscopic sense, although its macroscopic appearance is that of a smooth surface. The metal does not fill up the pores of the porous support sheet nor does it impede the permeability inherent to the porous sheet. In addition to being permeable to fluids, the porous metal film possesses a radiation-blocking effect which is the result of the radiation-blocking property of metal and is therefore characterized by a satisfactory radiation-blocking effect even when a small amount of metal is used (i.e., a thin layer) and can be contrasted with the conventional white pigment powders which are light permeable in nature.

In addition, according to the description of the above-mentioned references, when a colored reagent is used in the reagent layer it is necessary to block out the color lest it should interfere with a quantitative colorimetric assay. In this case the radiation-blocking layer is positioned between the reagent layer and the observation side of the support, for example, the radiation-blocking layer is provided beneath the colored reagent layer (i.e., in contact with the surface of the colored reagent layer distant the porous spreading layer). In other words, a porous metal film supported on a porous sheet of a thickness of several ten μm is formed separately and arranged as layer 6 in FIG. 2 beneath the colored reagent layer 8 and the quantitative chemical analysis is made by the colorimetric examination of the detecting layer 5 in which the color change is registered. When a white pigment such as barium sulfate is used as the radiation-blocking agent, a special technique for manufacture is required to give the layer a thickness of about 150 μm or more and to a porosity to secure the water permeability of the layer.

The reagent layer contains one or more materials which reacts with the factor to be analyzed, a precursor or reaction product thereof to produce a detectable species. The particular active material in the reagent layer will depend upon the factor to be analyzed. In the case of many analyses enzymes such as oxidase materials may desirably be included within the reagent layer as interactive materials. Materials or compositions that contain an oxidizable material and can provide a detectable species upon reaction with or in the presence of the factor to be analyzed, a precursor or reaction product thereof can also be used and include certain dye-providing compositions including auto-coupling compounds as are well known. In other aspects, the detectable species can be provided by oxidation of a leuco dye to provide the corresponding dyestuff. These and other reagents are disclosed in U.S. Pat. No. 4,042,335.

The multilayered integral element for the chemical analysis of the blood in accordance with the above embodiment of the present invention will be explained in detail with particular reference to the embodiments illustrated in the Figures.

FIG. 1 is an example of an analytical element constructed of a single reagent layer in which a reagent layer 2 is superposed on a transparent support 1 and a porous spreading layer 4 having a radiation-blocking layer 3 is intimately laminated thereon and set between the porous spreading layer and the reagent layer. In this case, the transparent support can be omitted if desired, and as mentioned above, the reagent layer can be composed of several layers to divide its functions. The porous metal film of the lower surface of the porous spreading layer can be placed on the top surface (i.e., on the surface of the porous spreading layer distant the reagent layer) or the porous spreading layer can have porous metal film on both surfaces. In an actual chemical analysis for the blood, a blood sample dropped from the direction depicted by Arrow A diffuses uniformly during the passage through the porous spreading layer and the liquid reaches and permeates into the reagent layer without change in chemical composition. In the reagent layer 2, a specific color developing reaction occurs to manifest a color density in proportion to the amount of the particular component of blood, and accordingly a quantitative colorimetry can be conducted by a reflection method from the direction depicted by Arrow B. Furthermore, because the surface of the porous metal film is light reflective, the radiation-blocking layer according to the present invention serves as a good background for quantitative colorimetry.

Figure 2:
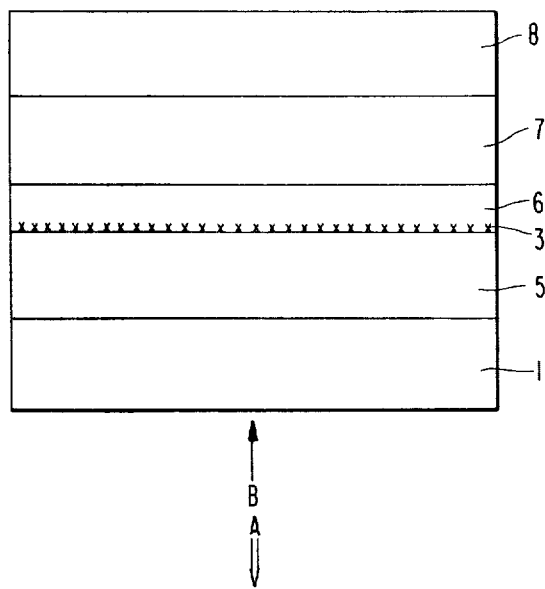

FIG. 2 shows an example of an analytical element having a plurality of reagent layers, especially that using a colored reagent. On a transparent support 1 are laminated a detecting layer 5, a porous sheet-like support 6 having a radiation-blocking layer 3, a colored reagent layer 7 and a porous spreading layer 8 in that order. In either case, an opaque or translucent support can be used if the support 1 is formed so as to be releasable from the detecting layer 5. The detecting layer is a layer in which color or any detectable form of a compound is registered for colorimetric or other measurement. Any layer which can absorb the detectable species (it is not necessary that the layer absorb 100% of the detectable species) formed in the reagent layer can be used. The detecting layer must be permeable to the detectable species but not necessarily be reactive or interactive with the species. Where the detectable species is a dye or other mordantable material, the detecting layer may contain a mordant, such as those described as useful image dye mordants in color photographic films and papers.

One general method for forming a porous metal film in accordance with this embodiment of the invention is to fabricate a porous sheet as a support using known materials such as membrane filter, rice paper, filter paper, Japanese paper, porous powder film, etc., and then to form a metal film thereon by electrolessly plating, metal depositing, etc.

It is most preferable to use the porous spreading layer itself which is one of the constituents of the elements for the chemical analysis of the blood according to the present invention as the support, i.e., the porous sheet. In this case, a porous metal film is formed on one surface of a porous spreading layer such as of membrane filter and subsequently it is laminated on and adhered to a reagent layer to integrate the two.

The metals which can be employed in the radiation-blocking layer include platinum, gold, silver, nickel, chromium, aluminum, zinc, tin, copper and the like and alloys and mixtures thereof. The metals which do not have a distinctive color are preferred.

The method for forming a porous metal film will be explained in detail with reference to a particular embodiment.

A membrane filter which is useful as a porous spreading layer (e.g., Microfilter FM or FR 300 manufactured by Fuji Photo Film Co., Ltd.) is chosen as a porous support and aluminum is vacuum deposited on one surface of the membrane filter thus giving a porous metal film thereon. Since it is difficult to determine the thickness of the metal film deposited on the membrane filter by actual measurement, the thickness of the film as indicated by a thickness monitor integrated in a vacuum deposition apparatus is regarded as the thickness of the film. If the thickness exceeds about 1,000 Å, the filtration rate of water or aqueous solutions tends to decrease and the filtering properties inherent to the membrane filter will change, thus lowering the function as the spreading layer. On the other hand, with a thickness of about 50 Å or less, the radiation-blocking effect is not adequate. Based on this fact, it has been found empirically that the thickness of the deposited metal film to be used as a radiation-blocking layer can range from about 50 Å to about 1,000 Å, preferably from about 50 Å to about 500 Å. In this manner, optimum conditions for forming the porous metal film on the porous sheet support can be attained experimentally.

In accordance with another embodiment of this invention, the radiation-blocking layer is a layer of a metal powder dispersed in an appropriate binder material. The metals which can be employed include platinum, gold, silver, nickel, chromium, aluminum, zinc, tin, copper, alloys and mixtures thereof and the like, with the white ground metals being preferred. Their shapes can be spherical, polyhedric, foil-like (i.e., thin sheet like platelets), etc. The size of the metal powder may be up to about half the thickness of the radiation-blocking layer and thus depends on the thickness of the layer. In the case of foil powder, it is appropriate to regard the size of the powder as the maximum dimension of the platelet and the size of the powder on this basis may be up to about the thickness of the radiation-blocking layer. The size of metal powder ranges generally from about 1 $\mu$m to about 20 $\mu$m in diameter. In a more particlar and preferred embodiment the powder is aluminum foil powder of about 1 $\mu m^2$ to about 50 $\mu m^2$ in area and of about 2 $\mu$m or less in thickness.

The radiation-blocking layer can be applied by coating a dispersion of a metal powder such as gold, silver, aluminum, zinc or the like in an appropriate binder material. Suitable binders include a hydrophilic binder such as gelatin or a composite mixture in which a hydrophobic binder such as a cellulose ester is dispersed and which provide a porous structure upon drying. Suitable examples of binders which can be used for the radiation-blocking layer of the present invention include water-soluble binders such as gelatin, agar, alginate, carboxymethyl cellulose, methyl cellulose, dextrin, etc., synthetic hydrophilic binders such as polyvinyl alcohol, polyvinyl pyrrolidone, polyacrylamide, etc., copolymers containing, e.g., acrylic, methacrylic, maleic, styrene sulfonate, etc., hydroxyethyl methacrylate, and the like. The coating composition is coated in a thickness such that after drying the thickness of the layer is about 2 $\mu$m to about 50 $\mu$m and dried. A suitable ratio for the amount of metal powder to the amount of binder in the radiation-blocking layer of the present invention ranges from about 100:1 to 1:100, preferably 10:1 to 1:10, by weight. As the metal powder, particulate powder and foil powder can be suitably used, especially foil powder has proved to possess a good radiation-blocking effect and it was found that in such case the radiation-blocking layer having a thickness of about 2 $\mu$m to about 20 $\mu$m is adequate and therefore that it gives a good permeability to water.

Figure 3:
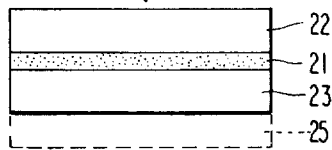

FIG. 3 is a cross-section of an analysis element in which a radiation-blocking layer 21 containing a metal powder dispersed in a binder is arranged between a porous spreading layer 22 and a reagent layer 23, and the blood is applied dropwise from the direction indicated by Arrow A and a quantitative analysis by colorimetry is conducted from the direction indicated by Arrow B.

Figure 4:
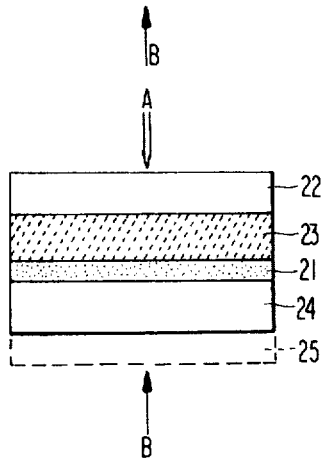

FIG. 4 is a cross-section of an analysis element having a plurality of reagent layers and illustrates the embodiment of the invention in which the radiation-blocking layer resides between the reagent layers. This element is constructed of a porous spreading layer 22, a first reagent layer 23, a radiation-blocking layer 21 and a second reagent layer or other functional layer 24 in that order. Particularly when the first reagent layer 23 is considerably colored by a colored material, the radiation-blocking layer must reside in this place. The dotted line 25 designates the optional presence of a support in both FIGS. 3 and 4.

The multilayered integral element for the chemical analysis of the blood in accordance with the present invention comprises the porous spreading layer, the reagent layer and the radiation-blocking layer as essential elements (layers), but the material may further contain one or more other elements suitably selected from a support, a water evaporation blocking cover which can be released from the porous spreading layer, a waterproof layer having at least one opening and a filter layer as necessary, i.e., according to the requirements based on the use, the analytical equipment and method used, the operation conditions, the materials making up each layer, etc.

When a support is employed, it is provided in contact with the surface of the reagent layer opposite the porous spreading layer. If the unit has a plurality of reagent layers, a transparent support is provided in contact with the surface of the reagent layer most distant from the side on which a blood sample is dropped and opposite the porous spreading layer. The transparent support may be a film transmitting near ultraviolet light, visible light and near infrared light, such as of polyesters (e.g., polyethylene terephthalate), polycarbonates (e.g., polycarbonates of bisphenol A), cellulose esters (e.g., cellulose diacetate, cellulose triacetate, cellulose acetate propionate, cellulose acetate butyrate, etc.), etc., having a thickness of about 10 $\mu$m to about 0.5 mm. Alternatively, an opaque paper coated with a releasing agent such as a silicone resin or a transparent, translucent or opaque tape of a polymer film can be adhered to the reagent layer as a support. When the support coated with a releasing agent is used, it functions as a protective layer for the element for the chemical analysis of the blood and the actual measurement can be conducted after peeling it off.

When the water evaporation blocking cover which can be released from the porous spreading layer is used, this water evaporation blocking cover is so arranged as to cover the entire porous spreading layer. The shape, material, mode of arrangement, etc., can follow the description in Japanese Utility Model Application No. 59886/78.

The waterproof layer having at least one small opening is provided in contact with the surface of the porous spreading layer distant from the reagent layer. The shape, size and number of the openings, the shape, material, mode of arrangement, etc., of the waterproof layer can follow the description in Japanese Utility Model Application No. 59888/78 (U.S. Patent application Ser. No. 35,182, filed May 2, 1979).

When the filter capable of removing the definitely-shaped components of blood is used, the filter layer is provided in contact with the surface of the waterproof layer the other surface of which is in contact with the porous spreading layer. The shape, material, mode of arrangement, etc., of the filter layer capable of removing the definitely-shaped components of blood can follow the description in Japanese Utility Model Application No. 77177/78 (U.S. Patent Application Ser. No. 46,125, filed June 6, 1979). Further, the filter layer can also be provided in contact with the surface of the porous spreading layer distant from the reagent layer, in such case, the water evaporation blocking cover or the waterproof layer having opening or openings may be arranged to cover the filter layer (i.e., the surface of the filter layer not in contact with the porous spreading layer).

In order to manufacture the element for the chemical analysis of the blood in accordance with the present invention generally a reagent layer is formed on a transparent support by coating followed by integration by laminating thereon a separately fabricated porous spreading layer having a porous radiation-blocking layer in accordance with the present invention. Alternatively, as in the case with a colored reagent, a color detecting layer is provided on a support by coating, a separately fabricated porous sheet having a porous metal containing radiation-blocking layer is provided thereon and finally a colored reagent layer and a porous spreading layer are superposed thereon by coating or laminating.

The multilayered integral element for the chemical analysis of the blood which has the radiation-blocking layer of the present invention does not impede the permeability to moisture. The radiation-blocking layer in accordance with the present invention, even when the layer is used in the wet state, does not exhibit any problems of decrease in radiation-blocking effect, from which the conventional radiation-blocking layers using barium sulfate, titanium oxide, etc., have been suffering. In addition, because the surface of the metal powder is light reflective, the radiation-blocking layers of the present invention can serve as good background for colorimetry of color developed images.

Furthermore, with the multilayered integral elements for the chemical analysis of the blood which have the radiation-blocking layer containing a metal according to the present invention, a colored reagent can be used as the reagent, and when whole blood is used as a blood sample, its color can be completely blocked. Especially, since this radiation-blocking effect is good even where the analysis element is used in the wet state, a quantitative analysis by, e.g., colorimetry can be conducted immediately after the color spreading reaction in the aqueous system without any drying operation, thus rendering the rapidness of the multilayered integral element for the chemical analysis of the blood much more advantageous. Since a thickness of about 20 $\mu$m or less is substantially adequate as the radiation-blocking layer because of its good radiation-blocking effect, the drying of the coating in manufacture is much simplified as compared with the prior art elements and the analysis is efficiently conducted because the radiation-blocking does not inhibit the permeability to blood. In addition, the process for manufacture thereof is greatly simplified as compared with that of the conventional porous radiation-blocking layers using white pigments which require special technique to give the desired thickness.

EXAMPLE 1

This example illustrates a multilayered integral element for the chemical analysis of the blood for determination of glucose level in blood. A film of polyethylene terephthalate (hereinafter referred to as PET) of a thickness of 170 $\mu$m coated with a photographic, hydrophilic undercoat was coated with a reagent layer composition having the following formulation in the prescribed amounts per unit area (m$^2$) as a gelatin aqueous solution and dried to give a reagent layer.

| Coating Composition for the Reagent Layer | |
|---|---|
| 10 Weight % Gelatin Aqueous Solution | 210 g |
| Sodium 1-Naphthol-2-sulfonate | 1 g |
| 4-Aminoantipyrine | 0.52 g |
| Glucose Oxidase | 13,000 units |
| Peroxidase | 6,700 units |
| Nonionic Surfactant | 3 g |
| Glycerine | 30 g |

The pH was adjusted to 6.5 by the addition of NaOH.

Then, a dispersion for a light diffusion layer having the following formulation was coated on the reagent layer and dried to laminate the light diffusion layer having a thickness after drying of 15 $\mu$m.

| Composition of the Dispersion for the Light Diffusion Layer | |
|---|---|
| 10 Weight % Gelatin Aqueous Solution | 30 g |
| Barium Sulfate | 10 g |

In the meantime using a vacuum deposition apparatus, an aluminum layer of a thickness of about 200 Å was deposited on a membrane filter (Microfilter FM-300 manufactured by Fuji Photo Film Co., Ltd.) size A-4 (21 cm$\times$29.7 cm) and 150 $\mu$m in thickness at the outlet face under a vacuum of 1$\times$10$^{-6}$ Torr. The aluminum used was in the form of wire of 2 mm in diameter and it was placed in a helical coil of tungsten and heated to 1,100° C. The thickness of the deposited film was measured by a quartz oscillating film thickness monitor. The microfilter thus prepared and having an aluminum-deposited metal film was laminated on the light diffusion layer with its aluminum layer inside to serve as a porous spreading layer while the light diffusion layer was still wet and integrated by laminating and adhering to prepare Sample A.

On the other hand, Sample B was prepared by coating a dispersion for a radiation-blocking layer having the following formulation on the light diffusion layer and dried to provide the radiation-blocking layer having a thickness after drying of 15 μm.

| Radiation-Blocking Layer Composition | |
|---|---|
| 10 Weight % Gelatin Aqueous Solution | 160 g |
| Aluminum Foil Powder (amorphous shape; size of about 6 μm on the average) | 3 g |

After wetting the surface of the radiation-blocking layer with water, a membrane filter having a thickness of 15 μm and a pore size of 1.2 μm (Microfilter 120 manufactured by Fuji Photo Film Co., Ltd.) was laminated thereon and bonded to form a porous spreading layer, thus fabricating a multilayered integral element for the chemical analysis of the blood.

Using the multilayered integral elements for the chemical analysis of the blood having a radiation-blocking layer comprising a porous metal-containing film and a metal powder dispersion respectively prepared as above, 10 μl of whole blood was dropped on its porous spreading layer to permit it to spread and was observed from the PET film side to find no red color attributed to the blood. In the reagent layer there was observed a color development reaction the color density of which corresponded to the glucose level in blood.

COMPARISON EXAMPLE 1

As a comparison, a conventional multilayered integral element for the analysis of the blood was prepared according to the description of Example 1 in Japanese Patent Application (OPI) No. 40191/76 (U.S. Pat. No. 4,042,335). In this element, the radiation-blocking layer was composed of a white pigment (titanium dioxide dust) dispersed in gelatin. In order to secure the perfect radiation-blocking effect, it was necessary to give the layer a thickness of about 150 μm (ten times that of the radiation-blocking layer according to the present invention). In addition, it was found that greater amount of blood sample and more time were necessary to permit the permeation of the blood components through such a thick layer as compared with the elements of the present invention.

Figure 5:
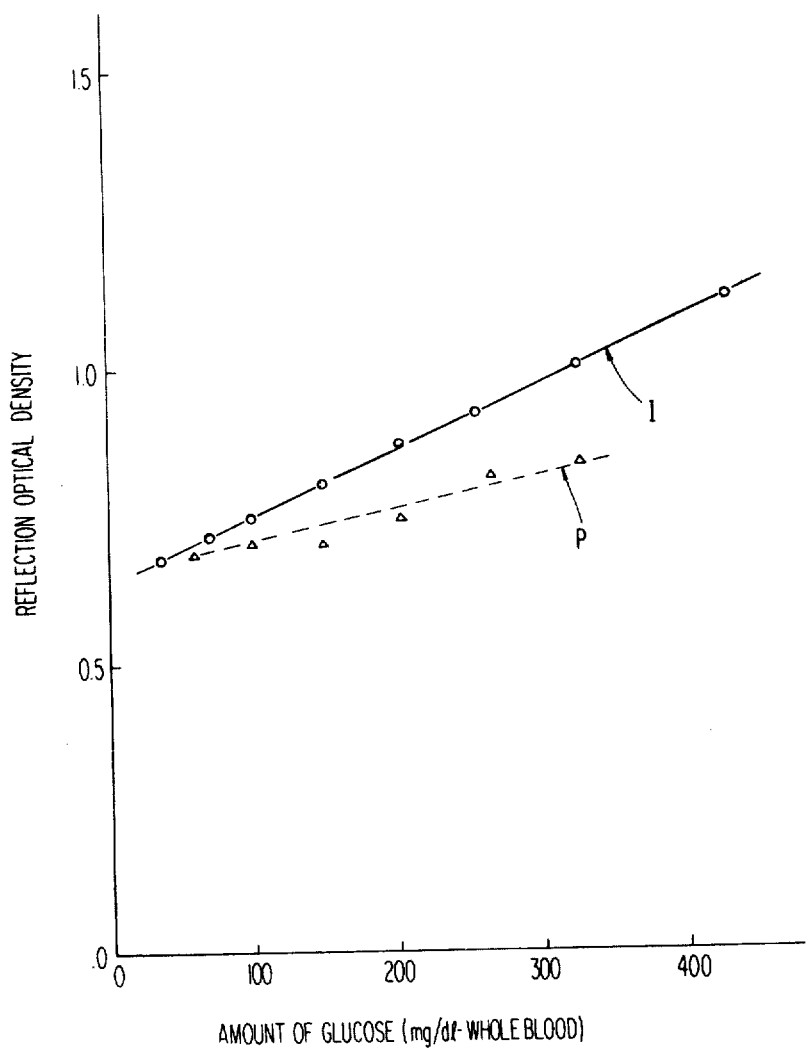
FIG. 5 is a comparison of calibration curves for an element prepared in accordance with the present invention and a comparison element.

The results of the quantitative analyses of glucose levels in blood using whole blood as blood samples on Sample B in the multilayered integral element for the chemical analysis of the blood according to the present invention described in Example 1 and the conventional multilayered integral element for the chemical analysis of the blood are shown in FIG. 5. In the Figure, the line I representing the element for the chemical analysis of the blood according to the present invention shows good quantitativeness whereas line P representing the conventional element for the chemical analysis of the blood gives appreciably poor quantitativeness. (Conditions: blood amount for each run 10 μl, 30° C., 10 minutes after the dropping the concentration of the color development was measured on a Macbeth densitometer using a green filter).

EXAMPLE 2

The procedures in Example 1 was repeated except that the light diffusion layer was omitted and observed from the PET film side to obtain similar results to those of Example 1.

EXAMPLE 3

This example illustrates a multilayered integral element for the chemical analysis of the blood for determination of amylase level using a colored reagent.

On a PET film similar to that in Example 1 was applied a detecting layer containing 3 g/m² of gelatin and 2 g/m² of a mordant (a copolymer of styrene and N,N-dimethyl-N-(3-maleimidopropyl)ammonium chloride) by coating. A radiation-blocking layer containing aluminum foil powder and having a thickness after drying of 20 μm was applied thereon in a manner similar to that of Sample B in Example 1. Further laminated thereon was a membrane filter similar to that in Sample B of Example 1 which had been impregnated with a colored reagent of a dye-combined amylopectin solution (Reaction Red 2B Amylopectin supplied by General Diagonostics Co., U.S.A.) as a substrate for amylase enzyme and dried to obtain a multilayered integral element for the chemical analysis of the blood for determination of amylase level in blood. This element had a structure in which the reagent layer and the spreading layer were integrated.

This element completely blocked the color of the colored reagent when observed from the PET film side and when it was tested using an amylase standard solution, the dye was received only by the detecting layer where the standard solution was dropped thus successfully permitting a quantitative analysis by colorimetry from the PET film side.

As described above, the water-permeable radiation-blocking layers containing metal powder in accordance with the present invention have a satisfactory radiation-blocking effect with a thickness about one tenth that of the conventional radiation-blocking layers, and accordingly the overall thickness of the multilayered integral element for the chemical analysis of the blood could be reduced thus showing great improvement in manufacture of the elements and performance of the chemical analysis.

While the invention has been described in detail and with reference to specific embodiments thereof, it will be apparent to one skilled in the art that various changes and modifications can be made therein without departing from the spirit and scope thereof.

What is claimed is:

1. An integral multilayered element for the chemical analysis of the blood comprising a combination of a porous spreading layer, a reagent layer, and a radiation-blocking layer, said radiation-blocking layer being water-permeable and containing at least one elemental metal or an alloy thereof.

2. The element of claim 1, wherein said metal is selected from the group consisting of platinum, gold, silver, nickel, chromium, aluminum, zinc, tin, and cooper and alloys and mixtures thereof.

3. The element of claim 1, wherein said element comprises a porous spreading layer, a radiation-blocking layer and a reagent layer laminated in that order.

4. The element of claim 1, wherein said element comprises a support having laminated thereto in order a reagent layer, a radiation-blocking layer and a porous spreading layer.

5. The element of claim 1, wherein said element comprises a detecting layer, a radiation-blocking layer, a reagent layer and a porous spreading layer in that order.

6. The element of claim 1, wherein said element comprises a support having laminated thereto in order a detecting layer, a radiation-blocking layer, a reagent layer, and a porous spreading layer.

7. The element of claim 1, wherein said radiation-blocking layer is positioned on one surface of said porous spreading layer.

8. The element of claim 1, which further comprises a water evaporation blocking cover releasably mounted on the surface of the porous spreading layer which is opposite the surface nearest the reagent layer.

9. The element of claim 1, wherein said radiation-blocking layer is a porous metal film.

10. The element of claim 9, wherein said porous metal film is about 50 to about 1,000 Å thick.

11. The element of claim 1, which further comprises a waterproof layer in contact with the surface of the porous spreading layer opposite the surface which is nearest the reagent layer.

12. The element of claim 11, which further comprises a filter layer interposed between said waterproof layer and said porous spreading layer.

13. The element of claim 1, wherein said radiation-blocking layer is a layer of a metal powder dispersed in a binder.

14. The element of claim 13, wherein said metal powder has a particle size of about 1 to 20 $\mu$m.

15. The element of claim 13, wherein said metal powder is an aluminum platelet about 1 to 50 $\mu m^2$ in area and about 2 $\mu$m or less in thickness.

16. The element of claim 13, wherein the weight ratio of said metal powder to said binder is about 100:1 to 1:100.

* * * * *